US 9,398,853 B2

United States Patent
Nanikashvili

(10) Patent No.: US 9,398,853 B2
(45) Date of Patent: Jul. 26, 2016

(54) COMMUNICATION TERMINAL, MEDICAL TELEMETRY SYSTEM AND METHOD FOR MONITORING PHYSIOLOGICAL DATA

(75) Inventor: Reuven Nanikashvili, Rechovet (IL)

(73) Assignee: LifeWatch Technologies, Ltd., Rehovot (IL)

( * ) Notice: Subject to any disclaimer, the term of this patent is extended or adjusted under 35 U.S.C. 154(b) by 2848 days.

(21) Appl. No.: 11/144,891

(22) Filed: Jun. 3, 2005

(65) Prior Publication Data

US 2007/0015973 A1   Jan. 18, 2007

(51) Int. Cl.
*A61B 5/00*    (2006.01)
*G06F 19/00*   (2011.01)
*A61B 5/02*    (2006.01)

(52) U.S. Cl.
CPC ............... *A61B 5/002* (2013.01); *G06F 19/32* (2013.01); *A61B 5/02* (2013.01)

(58) Field of Classification Search
CPC ... A61B 5/00; G06F 19/3418; G06F 19/3431; G06F 19/322; G06F 19/3487; G06F 19/3406; G06F 19/3468; G06F 19/3475; G06F 19/3481; H04H 20/40; H04H 60/32; H04L 1/0057
USPC ........................... 600/300–301; 128/903–904; 340/539.12; 705/2–4
See application file for complete search history.

(56) References Cited

U.S. PATENT DOCUMENTS

| | | | |
|---|---|---|---|
| 6,749,566 B2 * | 6/2004 | Russ ............................. | 600/300 |
| 7,009,511 B2 * | 3/2006 | Mazar .................. | A61B 5/0031 340/531 |
| 7,197,366 B2 * | 3/2007 | Bodin et al. .................... | 700/90 |
| 7,292,139 B2 * | 11/2007 | Mazar .................. | A61B 5/0031 340/531 |
| 7,606,617 B2 * | 10/2009 | Wariar ............... | A61B 5/14507 607/17 |
| 7,791,467 B2 * | 9/2010 | Mazar .................. | A61B 5/0031 340/531 |
| 8,130,093 B2 * | 3/2012 | Mazar .................. | A61B 5/0031 340/531 |
| 8,246,563 B2 * | 8/2012 | Wariar ............... | A61B 5/02405 210/646 |
| 8,451,113 B2 * | 5/2013 | Mazar .................. | A61B 5/0031 340/531 |
| 8,740,789 B2 * | 6/2014 | Brockway ................ | A61B 5/00 128/920 |
| 8,791,815 B2 * | 7/2014 | Mazar .................. | A61B 5/0031 340/531 |
| 9,232,903 B2 * | 1/2016 | Pless ................... | A61N 1/36064 |
| 2003/0212311 A1 * | 11/2003 | Nova et al. ..................... | 600/300 |
| 2004/0102685 A1 * | 5/2004 | Cosentino et al. ............ | 600/300 |
| 2004/0117204 A1 * | 6/2004 | Mazar et al. ...................... | 705/2 |
| 2006/0121846 A1 * | 6/2006 | Mazar .................. | A61B 5/0031 455/7 |

(Continued)

*Primary Examiner* — Gary Jackson
*Assistant Examiner* — Shirley Jian
(74) *Attorney, Agent, or Firm* — Reches Patents

(57) ABSTRACT

A medical telemetry system for remote monitoring of data collected from mobile persons including a sensor capable of monitoring physiological data, a mobile communication telemeter operably connected to said sensor for communicating physiological data to terminals, a plurality of terminals for receiving physiological data and for communication said physiological data over a wireless link using the Bluetooth standard to a communication gateway, and a communications gateway for communicating such physiological data to a first end of a communications network. Terminal may also be operably connected to power lines and may be capable of transmitting data via both a wireless link and a power line modem over power lines, such that the power line modem is capable of communicating or receiving physiological data over power lines if it is unable to communicate physiological data over a wireless link.

14 Claims, 14 Drawing Sheets

(56) References Cited

U.S. PATENT DOCUMENTS

| | | | |
|---|---|---|---|
| 2006/0200007 A1* | 9/2006 | Brockway | A61B 5/00 600/300 |
| 2006/0247504 A1* | 11/2006 | Tice | 600/300 |
| 2007/0106129 A1* | 5/2007 | Srivathsa | A61B 5/0031 600/300 |
| 2007/0175827 A1* | 8/2007 | Wariar | A61M 1/1613 210/645 |
| 2007/0179389 A1* | 8/2007 | Wariar | A61B 5/14507 600/508 |
| 2008/0065416 A1* | 3/2008 | Mazar | A61B 5/0031 705/2 |
| 2010/0328062 A1* | 12/2010 | Mazar | A61B 5/0031 340/539.12 |
| 2012/0139720 A1* | 6/2012 | Mazar | A61B 5/0031 340/539.1 |
| 2013/0271279 A1* | 10/2013 | Mazar | A61B 5/0031 340/539.12 |
| 2016/0066816 A1* | 3/2016 | Pless | A61N 1/36064 600/302 |

* cited by examiner

COMMUNICATION TERMINAL, MEDICAL TELEMETRY SYSTEM AND METHOD FOR MONITORING PHYSIOLOGICAL DATA

FIELD OF THE INVENTION

The present invention relates to systems and methods for monitoring the health of one or multiple persons, especially within a building that includes multiple rooms.

BACKGROUND OF THE INVENTION

There are various types of physiological data types that can reflect the health of a person. Various physiological monitors are known in the art and include an electrocardiograph (ECG) monitoring device, a device for monitoring blood oxygen saturation, a device for monitoring respiration, a device for monitoring blood glucose, a device for monitoring blood pressure, a device for monitoring lung function, a device for monitoring SpO2 saturation, a device for monitoring temperature, a device for fat analysis, a fetal hart rate monitor device for pregnancy women, EEG device and the like. Each physiological monitoring device includes at least one sensor and may also include an analog component such as an analog amplifier, an analog comparator, an analog to digital converter and the like.

The monitoring devices can be fixed or mobile. Mobile monitoring devices can be carried by, mounted on worn by a client. Transmitting the gathered physiological data to remote locations can be expensive or highly complicated. The complexity can result from strict limitation upon the transmission power, from the multi-path phenomena and the like.

U.S. Pat. No. 6,773,398 of Flach et al., titled "cellular architecture and data transfer methods for real time person monitoring within a medical facilities", which is incorporated herein by reference, describes a complex system for transmitting physiological data over a hybrid network that includes multiple wireless transceivers (VCELLs) using a TDMA protocol and a RS-232 based twisted pair network for conveying the physiological data to a central unit and than to local network.

The system is very complex and requires to install dedicated communication links within the walls of the building, thus further increasing the cost of the system. Said installation is usually more expensive and time consuming in hospitals, as special safeguards must be taken to prevent direct or indirect damages to persons, oxygen supply lines and medical equipment. Furthermore, installing such a system in person homes is very expensive.

Therefore, there exists a need for an improved medical telemetry system for remote monitoring of data collected from mobile persons.

SUMMARY

A terminal for receiving physiological data over a wireless link and for transmitting said data over at least one power line. The terminal can be installed within a building and conveniently is capable of short range wireless communication with a mobile telemeter that in turn may receive the physiological data over wire or wireless links.

A system that includes multiple terminals that are connected to one or more computerized units such computers, display units, analysis stations storage stations and the like.

A method for providing physiological data that includes receiving over a wireless link physiological data and transmitting it over at least one power line.

According to an embodiment of the invention the physiological data can be processed, and in response can also be selectively transmitted.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1A:
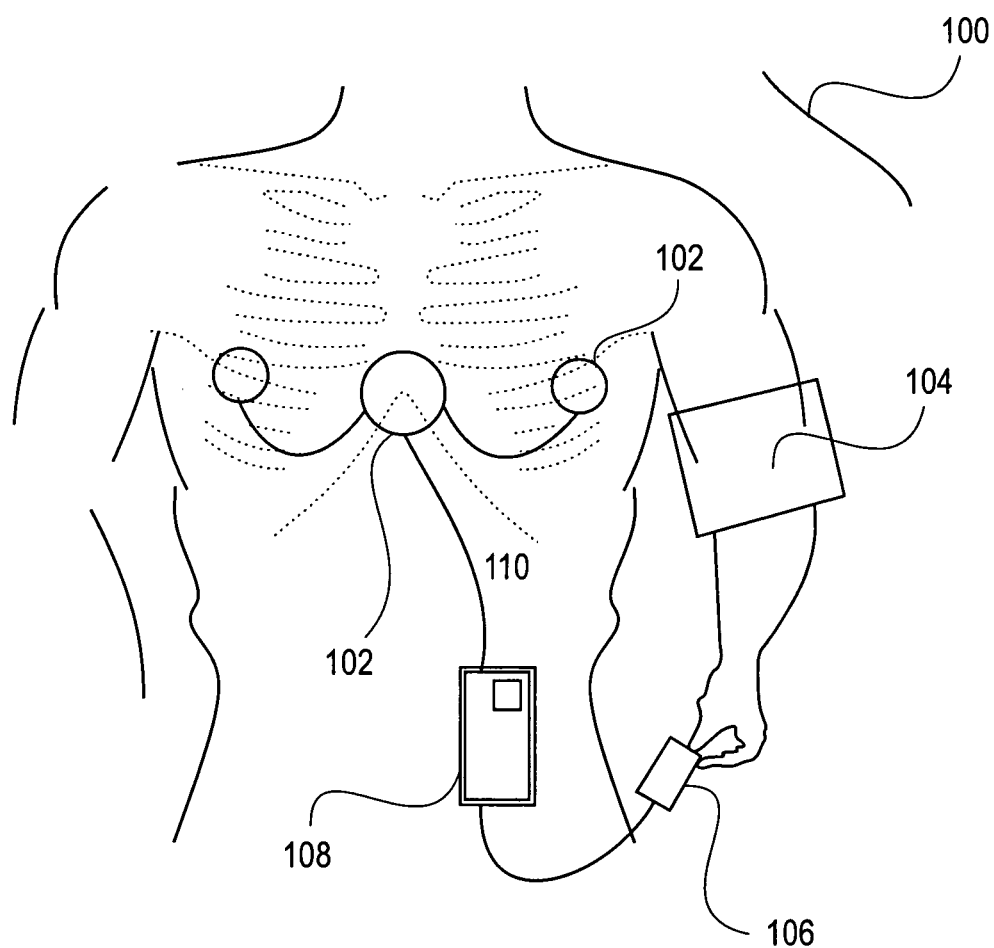
FIG. 1A illustrates sensors linked by wire to a mobile telemeter worn by an person in accordance with an embodiment of the invention.

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein.

Furthermore, well known features may be omitted or simplified in order not to obscure the invention.

Unless specifically stated otherwise, as apparent from the following discussions, it is appreciated that throughout the specification discussions regarding signal or data processing, or utilizing terms such as "controllers" "processing", "computing", "calculating", "determining", or the like, may refer to the action and/or processes of a data processor, computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, Flash memories, disks on key, disk on chip, or any other type of media suitable for storing electronic instructions, and capable of being coupled to a computer system bus.

The processes and displays presented herein are not inherently related to any particular computer, chipset, microchip, or other apparatus. Various general purpose systems may be used with programs in accordance with the teachings herein, or it may prove convenient to construct a more specialized apparatus to perform the desired method. The desired structure for a variety of these systems will appear from the description below.

The invention provides a terminal that includes: a wireless receiver, adapted to receive physiological data collected by at least one sensor; a power line transmitter, coupled to the wireless receiver, adapted to receive the physiological data and transmit, over at least one power line, the physiological data; and a terminal controller, coupled to the power line transmitter and the wireless receiver, for controlling the power line transmitter and the wireless receiver.

Conveniently, at least one sensor is coupled to a short-range transceiver and whereas the terminal further comprises a wireless transmitter for transmitting signals to the short-range transceiver. Conveniently, the terminal according to claim 1 further adapted to receive physiological data from multiple persons simultaneously.

According to an embodiment of the invention the terminal controller is adapted to at least partially analyze the received physiological data and to decide whether to transmit said physiological data.

According to yet a further embodiment of the invention the terminal controller is adapted to at least partially process the received physiological data to provide processed physiological data. Conveniently, the terminal controller is further adapted to determine whether to transmit said physiological data.

According to an embodiment of the invention, the at least one sensor is coupled to a mobile telemeter adapted to at least partially process the received physiological data to provide processed physiological data.

Conveniently, the mobile telemeter is further adapted to determine whether to transmit said physiological data.

According to an embodiment of the invention, the terminal further includes an additional transmitter, for transmitting the physiological data over links other than power lines. Conveniently, the terminal is further adapted to determine whether to transmit the physiological data by the power line transmitter or by the other transmitter.

According to an embodiment of the invention the terminal is further adapted to temporarily store the physiological data.

According to an embodiment of the invention the terminal is further adapted to apply error corrections algorithms on a reception or on a transmission of the physiological data.

According to another embodiment of the invention the terminal is further adapted to apply acknowledge based transmission algorithms on a reception or on a transmission of the physiological data.

According to an embodiment of the invention the terminal is further adapted to limit a transmission of physiological data too instances wherein the physiological data varies from predefined physiological parameters.

The invention provides a health telemetry system, that includes multiple terminals adapted to wirelessly receive physiological data and to transmit, over at least one power line, the physiological data; and at least one computerized unit, adapted to receive at least a portion of the physiological data.

According to various embodiments of the invention the system can include terminals according to mentioned above embodiments.

According to another embodiments of the invention the terminals can be connected, by power lines and even by additional networks or communication links to various computerized units that can analyze the transmitted physiological data, display said data, send control signals or otherwise participate in the generation of the physiological data or its transmission. For example, a mobile telemeter 108 can initiate a physiological data gathering session in response to signals provided by a computerized unit.

The processing may include performing statistical analysis of gathered data, comparing acquired data or processed data to expected data, performing health event detection and the like.

The invention provides a method that include receiving, by a terminal, physiological data generated by one or more sensors, over a wireless connection, and transmitting the physiological data over at least one power line.

The term physiological data also includes data representative of a physiological condition of a person. This data can be processed, packetized or otherwise formatted according to various communication protocol, and the like.

Reference is hereby made to FIG. 1A which illustrates sensors linked by wire to a mobile telemeter worn by an person in accordance with an embodiment of the present invention. One or more sensors 102 such as for example, an ECG sensor, blood pressure sensor 104 or oximetry sensor 106, or other sensors may be worn or carried by an person 100. In other embodiments, such sensors 102 may be any sensor suitable for monitoring or testing physiologic person 100 data such as respiration rate, temperature or other physiologic functions. Sensor 102 may additionally sense and transmit various types of non-physiologic data, such as ECG loose-lead status data and person location data. Sensor 102 may be operatively by linked by wire 110 to a mobile telemeter 108 which may, for example, collect, format and packetize data from sensor 102. In certain embodiments of the present invention, the mobile telemeter 108 may be worn or carried by the person to whom sensor 102 is attached.

Figure 1B:
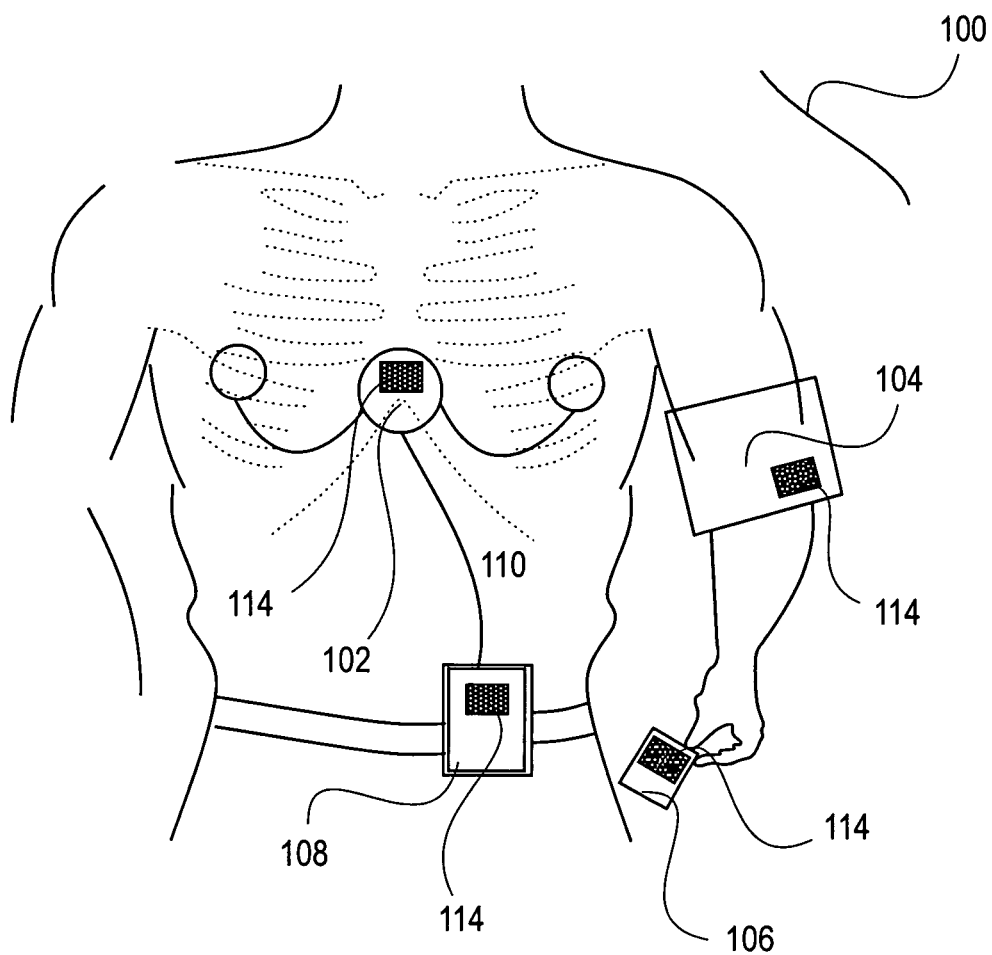
FIG. 1B illustrates sensors wirelessly linked to a mobile telemeter worn by an person in accordance with an embodiment of the invention.

Reference is made to FIG. 1B which illustrates sensors wirelessly linked to a mobile telemeter worn by an person in accordance with an embodiment of the invention. In FIG. 1B, each sensor such as for example, ECG sensor 102, blood pressure sensor 104 and oxymetry sensor 106 is fitted with a wireless transmitter device 114 that may be suitable for transmitting sensory data from sensors 102 to mobile telemeter 108. Such transmitter devices 114 may, for example, utilize the Bluetooth standard as is known in the art. Other transmitters may be used. Such wireless links may in certain embodiments reduce or alleviate the need for wires between sensor 102 and mobile telemeter 108.

Alternate embodiments of the system and method of the present invention may transmit medical data using the Bluetooth standard in different manners. For example, the Bluetooth standard may be used in a mobile medical telemeter system without intermediate devices between endpoints.

Figure 1C:
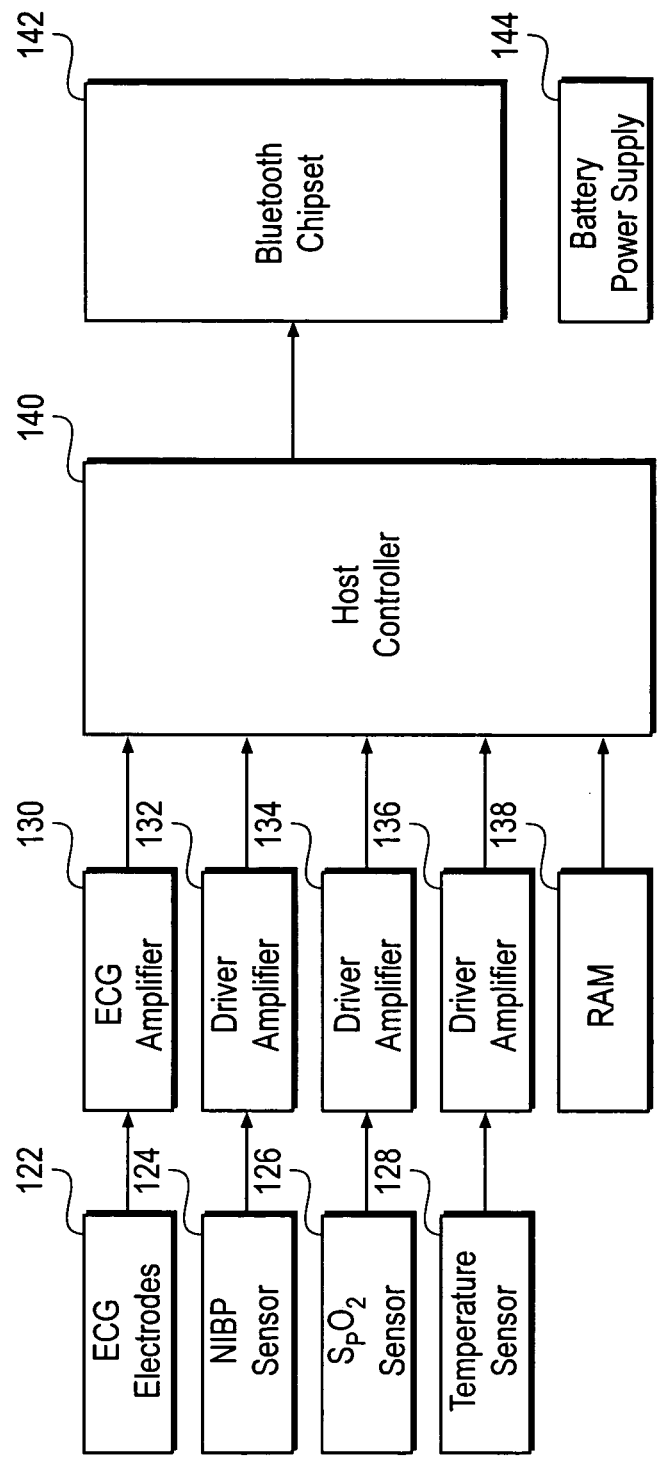
FIG. 1C is a schematic illustration of the components of sensors and a telemeter linked by wires in accordance with an embodiment of the present invention.

FIG. 1C is a schematic illustration of the components of sensors 102 and mobile telemeter 108 linked by wires in accordance with one embodiment of the present invention. Sensors 102, such as, for example ECG electrodes 122, NIBP sensor 124 and SpO2 sensor 126 typically include amplifiers 130 through 136 to amplify the readings collected by sensors 122 through 128. After being amplified, physiological data is transmitted by wires to controller 140. Controller 140 is capable of controlling the transmission of data from sensors 102 by, typically, Bluetooth Chipset transceiver 142. Other transmission methods, platforms and standards may be used. Controller 140 may in certain embodiments be a series of software instructions embedded in mobile telemeter 108. Other methods and systems may be used for controller 140. Controller 140 may in certain embodiments include a data storage unit to store data collected from sensors 102. Controller 140 may be connected to a power supply 144 such as a battery.

Figure 1D:
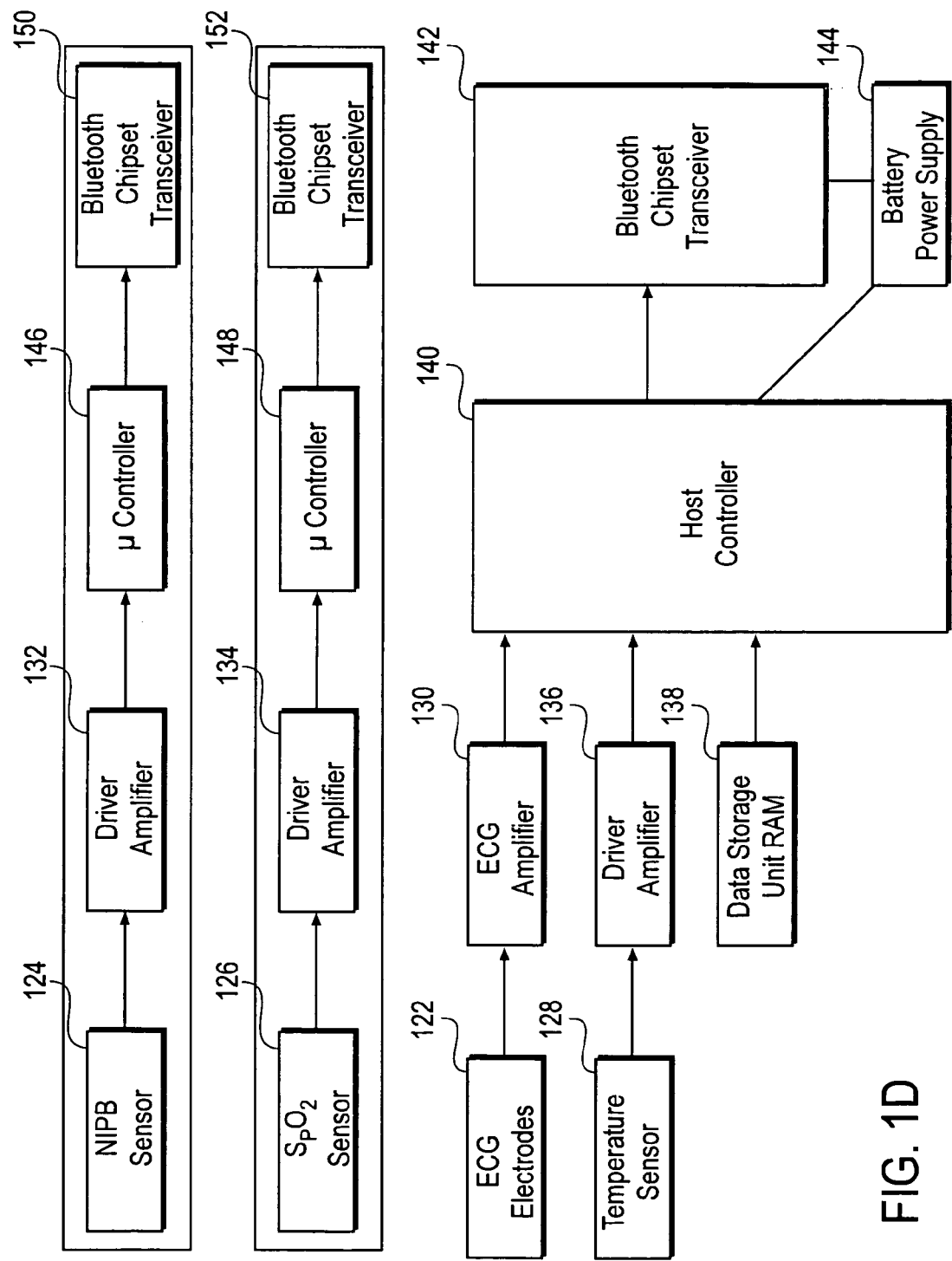
FIG. 1D is a schematic illustration of the components of sensors and a telemeter wherein certain sensors are linked by wire to a telemeter and other sensors are wirelessly linked to a telemeter in accordance with an embodiment of the present invention.

FIG. 1D illustrates a different configuration of the mentioned above components. Briefly, instead of having a single controller 140 and a single Bluetooth chipset, additional controllers 146 and 148, as well as additional chipsets 150 and 152 were added.

In certain embodiments of the present invention, controller 140 may be a microcontroller on which a Bluetooth protocol stack and application software are running. The application software may control, among other things, transceiver 142. In some embodiments, the application software may contain event-monitoring or detection software modules which may, for example, direct mobile telemeter 108 to transmit data or take other actions in the event physiological data collected by a sensor 102 varies from pre-defined parameters. For example, mobile telemeter 108 could be pre-programmed to transmit data or alert the person or a monitoring physician in the event that ECG readings from sensor 102 indicate arrhythmia or other cardiac abnormalities. In some embodiments such pre-defined parameters may be programmed into the application software of sensor 102. In certain embodiments, a data storage unit 138 is connected to controller unit 140 to store physiological data. Data storage unit 138 may be, for example, RAM, but may be another type of data storage unit, such as a disk drive. Data storage unit 138 may for example, store physiological data that is collected over long periods of time such as hours or even days and such data may be downloaded and evaluated at a later time, in a manner similar to that done with halter monitors as are currently known in the art. In other embodiments, data storage unit 138 may be used for short-term storage of collected physiological data. Such short term storage may be needed for example to evaluate collected physiological data against pre-defined physiologic parameters programmed into controller unit 140, or may be called upon for re-transmission by mobile telemeter 108 in the event that a prior transmission of such collected physiological data was interrupted or incomplete. When used for short term data storage purposes, data storage unit 138 can be constructed as a refreshable loop memory buffer that may be written over by subsequently collected physiological data. Other implementations of the controller unit 140 and other components may be used. For example, firmware or a computer on a chip may be used, and the Bluetooth standard need not be used.

In certain embodiments described below, collected physiological data may be stored in data storage unit 138 until telemeter 108 receives confirmation from an terminal, (such as an terminal 186 of FIG. 2 described below), that such physiological data was successfully transmitted and received by an terminal or by a central unit, such as central unit 184 of FIG. 2 described below. The data storage unit 138 may then store new physiological data by, for example, over-writing the old data.

Bluetooth chipset transceiver 142 is known in the art and includes such transceivers as are available from Cambridge Silicon Radio (CSR), such as the BlueCore-2 single chip system BC2120115A. Other transceiver systems may be used and may be based on other platforms and standards.

Some or all of mobile telemeter 108, sensor 102, Bluetooth chipset transceiver 142 and data storage unit 138 may be powered by battery power supply 144. Power supply 144 may be a disposable or rechargeable battery or other similar electrical power source. In alternative embodiments, sensor 102 may have any or all of its own power source and data storage unit. Other configurations of components of mobile telemeter 108 are also possible.

Figure 2:
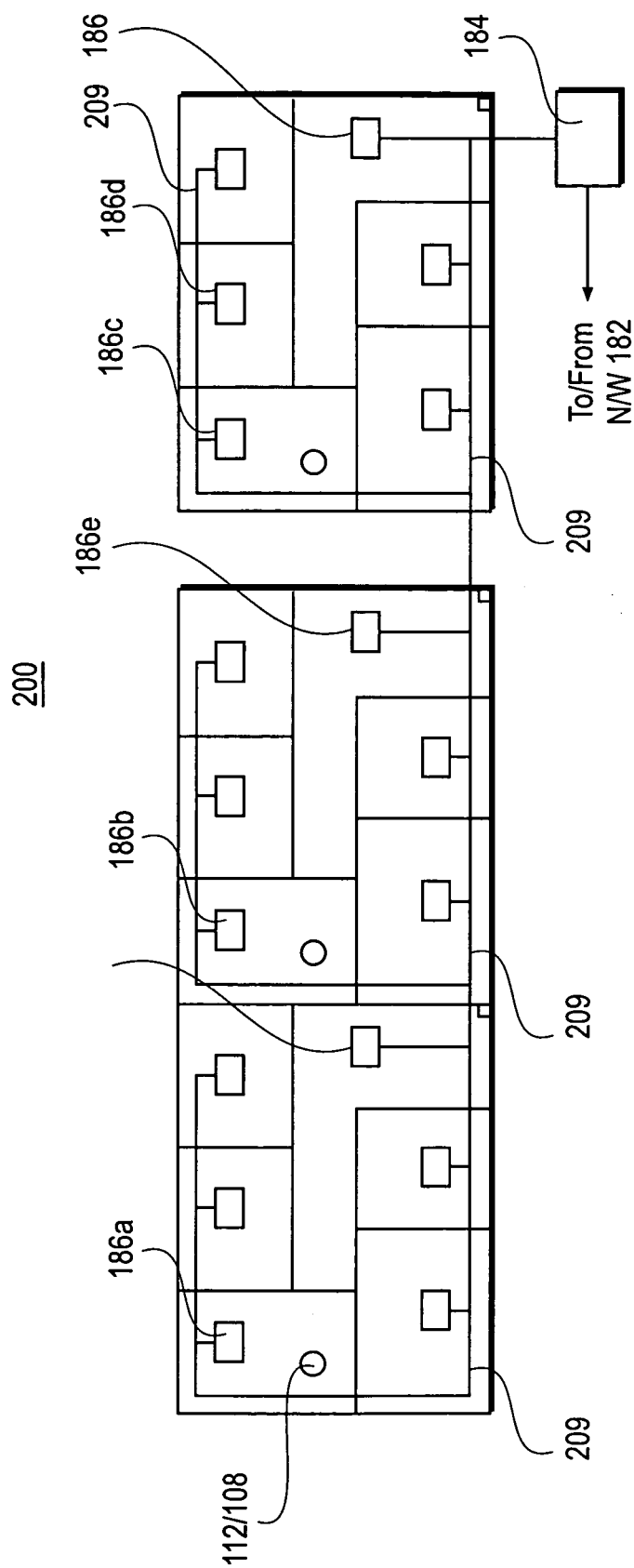
FIG. 2 is a schematic illustration of a person site coverage area in which the present invention may operate in certain embodiments of the present invention.

Reference is now made to FIG. 2, which illustrates a remote person site coverage area 200 in which the present invention may operate in certain embodiments. Open areas or rooms in coverage area 200 may be equipped with, for example, a terminal such as terminals 186a-186e, (collectively referred to as 186), or other communications terminal to receive and/or transmit physiological data. Terminal 186 may, for example, be affixed to a power line connector located on the wall or ceiling or otherwise located within a room or a corridor. Coverage area 200 may also contain a central unit 184 or other communication unit that may in certain embodiments of the present invention receiver data from multiple terminals, perform communication protocol conversions and act to a gateway. The central unit can be connected to one or more computerized units such as monitoring systems, display systems, local area networks, wide area networks, wireless networks and the like. Each terminal 186 can also receive physiological data from one or more persons using various prior art methods for multiple user communication. Physiological data received by terminal 186 may for example be the data collected by sensor 102 and transmitted by mobile telemeter 108. Terminal 186 may be connected to and powered by household power lines 209.

The communications link established between terminals 186 and central unit 184 can be deemed a short-range communications network as is known in the art. In the transmission of physiological data from mobile telemeter 108 to terminal 186, terminal 186 functions as master and mobile telemeter 108 serves as slave. In certain embodiments the present invention may be used to transmit data and voice signals.

In an embodiment of the invention, person 112 who may be equipped with a mobile telemeter 108 may move about within coverage area 200. As person 112 moves from room to room wearing mobile telemeter 108, mobile telemeter 108 typically transmits and/or receives data by wireless communication to and from terminal 186 in such a room. Transmission of such data is typically in the form of packetized physiological data along with, for example, ID codes of the respective mobile telemeter 108 that is transmitting. In a typical embodiment, terminal 186 transmits data either directly to central unit 184 or to another terminal 186 in the path to central unit 184. Central unit 184 may collect physiological data and transmit it to a gateway (not shown) for delivery onto a network 182.

In a typical embodiment of the present invention, a doctor, medical professional or medical data recording device may be connected or have access to a computerized unit such as a central station, as a PC in a hospital which is connected to network 182. Such doctor or other medical professional is thereby able to monitor such physiological data as it is retrieved from network 216. In other embodiments, network 216 may be a point-to-point communications network linking, for example, a person's home with a medical facility.

According to an embodiment of the invention a terminal 186 can also be adapted to perform wireless communication with network 184 or other devices. According to an embodiment of the invention the terminal can select between the two types of communication.

The wireless communication between terminals 186 and mobile telemeter 108 may in certain embodiments of the present invention embody Bluetooth technology and utilize Bluetooth standards and formats. Other data transmission formats may be used.

Data and voice signals may in certain embodiments flow from all or some of a central station to mobile telemeter 108 by way of central unit 184 and terminal 186, such that one way or two-way communication may be used in all or part of the present invention. Mobile telemeter 108 may in certain embodiments both receive and transmit voice data to and from one or more terminals 186.

Figure 3:
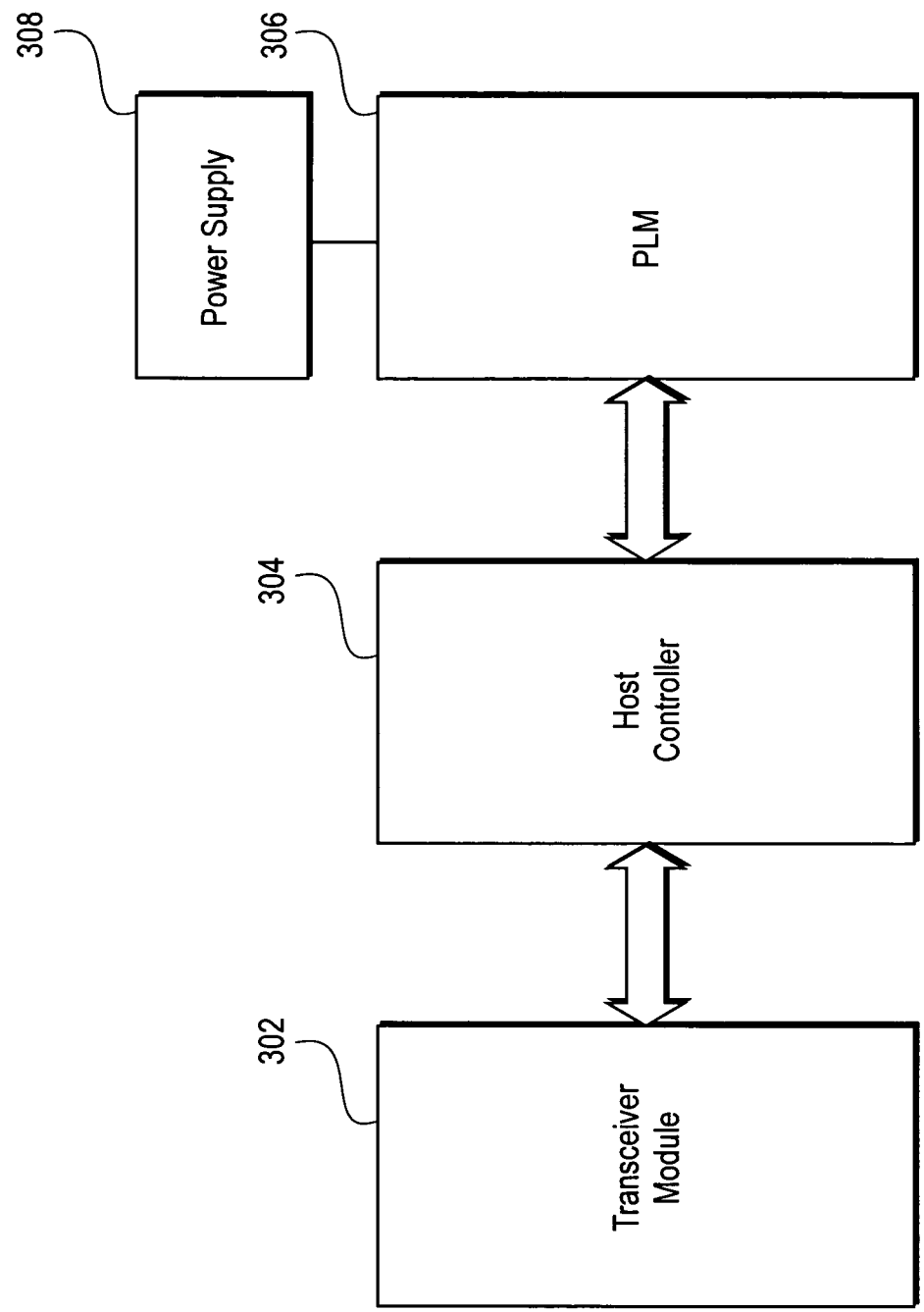
FIG. 3 is a simplified illustration of certain components of an terminal in accordance with an embodiment of the present invention.

Reference is made to FIG. 3, which is a simplified illustration of the components of terminal 186 in accordance with an embodiment of the present invention. In certain embodiments of the invention, terminal 186 includes a Bluetooth Chipset transceiver 302 for sending and receiving wireless signals, a power line modem (PLM) 306, and a terminal controller 304 which may in certain embodiments house the application software, the protocol stack and the software driver of power line modem 306. Power line modem 306 may be connected to power line 209, which may also provide operating power for terminal 186 and for other devices in the present invention. Power line modem 306 may be suitable for transmitting voice and/or data over power lines to which terminal 186 is connected. Power line modem 306 may be connected to power lines by a common two or three prong plug into a wall outlet, or by other methods. Power line modem 306 may be any embedded power line carrier (PLC) modem such as those available from Archnet ATL90115-1 or ATL90120-1. Bluetooth transceiver 302 may be a standard Bluetooth transceiver such as those available from Cambridge Silicon Radio (CSR) the BlueCore-2 single chip system BC2120115A. Terminal controller 304 may be a standard programmable microcontroller such as the ARM7TDMI from ARM Ltd. Company. Other configurations and models of the components of terminal 186 may also be used.

Power line 209 may be, for example, standard residential electric power lines of, for example, 110 volts, 220 volts or other voltage as may be in use, and may be connected to, for example, the local power grid (not shown). Connection of terminal 186 to power lines 209 may facilitate supplying power to the terminals 186 and central unit 184 as well as providing an additional medium of communication between terminals 186 and central unit 184 by way of power line communication through power line modem 306.

Figure 4:
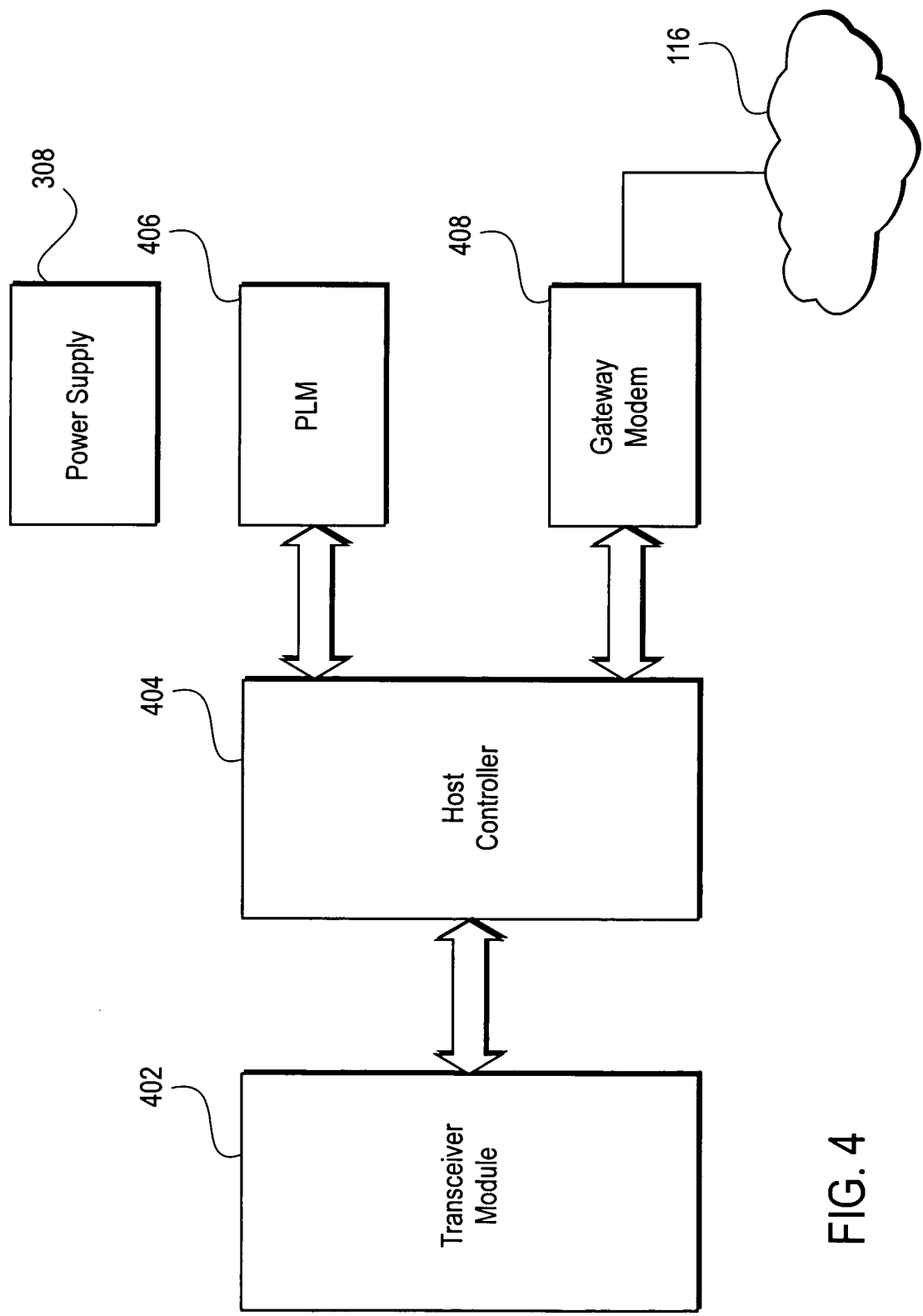
FIG. 4 is a simplified illustration of the components of a central unit in accordance with an embodiment of the present invention.

Reference is made to FIG. 4, which is a simplified illustration of the basic components of a central unit 184 in accordance with an embodiment of the present invention. Central unit 184 includes, for example, a Bluetooth chipset transceiver 402, a controller 404, and a power line modem 406. Power line modem 406 may be connected to power line 209 as described in FIG. 2. Such power line 209 may in certain embodiments also serve as a power source for central unit 184. In other embodiments, central unit 184 may be powered by a battery or other power source. Central unit 184 may in certain embodiments be connected to a gateway which may deliver data to network 116 as depicted in FIG. 2.

Bluetooth chipset 402 may be a Bluetooth transceiver chipset as are known in the art, such as the single chip BlueCore2 from Cambridge Silicon Radio (CSR). Controller 404, may be a standard programmable microcontroller as is known in the art such as ARM7TDMI from ARM Ltd. Company. Power line modem 406 may be suitable for transmitting voice and/or data over power lines to which central unit 184 is connected. Power line modem 406 may be an embedded power line carrier (PLC) modem such as those available from Archnet ATL90115-1 or ATL90120-1. Other configurations and models of such components of central unit 184 may also be used.

An embodiment of the present invention based on Bluetooth technology contemplates a single central unit 184 communicating with, in one embodiment, up to seven terminals 186 simultaneously. Similarly, using Bluetooth chipsets, terminals 186 may be able to communicate with, in one embodiment, up to seven mobile telemeters 108. Other numbers (and limits) of mobile telemeters 108 and terminals 186 that can be used with the present invention are also possible.

Figure 5:
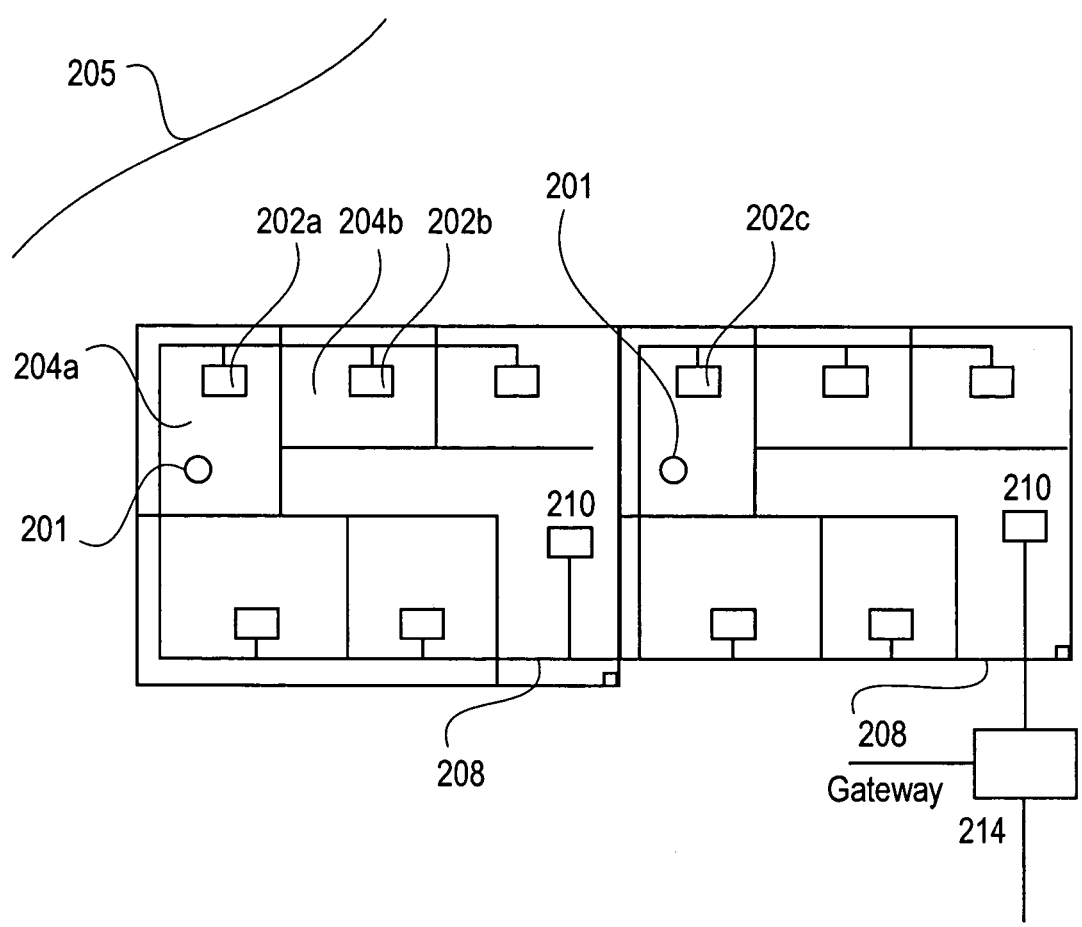
FIG. 5 is a simplified illustration of a large area of coverage in which an embodiment of the present invention may operate, in accordance with an embodiment of the present invention.

Reference is now made to FIG. 5, which is a simplified illustration of a relatively large area of coverage 205 of a wireless network with numerous rooms such as 204a and 204b and open spaces, in accordance with an embodiment of the present invention. In such large area of coverage 205, an terminal 186a may be too far away from central unit 184 to permit direct transmission of data or voice signals between them. Similarly, direct transmission may be not desirable or possible for other reasons such as for example, interference or bad signal quality. In such event, terminal 186a may transmit physiological data via other terminals such as 186b or 186c, which relay such signals to central unit 184. Other paths by which data or voice signals may be related from one terminal 186 to another in route to central unit 184 are also possible.

In certain embodiments of the present invention, terminal 186 may receive and transmit using multiple channels. Terminals 186 that are Bluetooth enabled may transmit and receive wireless data on, for example, up to seven channels simultaneously. Such a capability may allow a single terminal 186 to receive voice and data from up to seven mobile telemeters 108 simultaneously. Other limits or numbers of channels are possible.

As depicted in FIG. 5, to support person mobility, a number of terminals 186 may in certain embodiments of the invention be placed throughout a coverage area 205 to provide a "cell-like" coverage of the entire coverage area, consisting of overlapping zones of coverage. Such coverage may in certain embodiments permit the mobile telemeter 108 worn or carried by person to transmit to, and receive data from, at least one terminal 186 from anywhere in the coverage area 205. It is therefore possible that in certain embodiments of the present invention, a mobile telemeter 108 may transmit data to more than one terminal 186 at the same time. Similarly, it is possible that a single transmission of packetized data may be initiated between a mobile telemeter 108 worn or carried by a person and a particular terminal 186, but may be completed with another terminal 186. For example, referring to FIG. 5, a mobile telemeter 108 carried by person 201 moving from room 204*a* to room 204*b* may begin a transmission of physiological data to terminal 186*a*, then continue such transmission to both terminals 186*a* and 186*b* and finally end such transmission to terminal 186*b* alone. Other combinations are possible. controller software in central unit 184 may in certain embodiments of the present invention use error detection codes or other software to discard packets received in incomplete transmissions and/or duplicate packets received from more than one terminal 186. Embodiments of the present invention are thereby capable of supporting transmission by a mobile telemeter 108 while such mobile telemeter is moving from the transmission range of one terminal 186*a* into that of another terminal 186*b*, or when a mobile telemeter is within the transmission range of more than one terminal 186. Similarly, gateway 214 can be equipped with such error detection or duplicate packet detection capabilities to discard packets received in incomplete transmissions and/or duplicate packets received from more than one central unit 184.

Typically, controller layer software (reference numeral 134 of FIG. 1C) of mobile telemeter 108 supports temporary storage of data. Such temporary storage may in certain embodiments be called upon in the event that transmission of physiological data between a mobile telemeter 108 and an terminal 186 is interrupted, or in case there is a loss of data between mobile telemeter 108 and gateway 214. In that case, a repeat transmission of physiological data may be called from the data stored in the data storage unit 138 of mobile telemeter 108. Such storage and retransmission may in certain embodiments be controlled by software stored in controller 140 of mobile telemeter 108 as is depicted in FIG. 1C. Other components of the present invention such as central unit 184 or the terminal 186 may also call for repeat transmission of physiological data. In certain embodiments of the present invention, mobile telemeter 108 may be programmed to repeat a particular transmission until it receives confirmation of a successful receipt of such transmission from terminal 186, from central unit 184 or from gateway 214.

As illustrated in FIG. 5, the architecture of the present invention provides for a high degree of scalability. The present invention can initially be installed, for example, with a single central unit 184 which may in certain embodiments serve up to seven terminals 186. By adding an additional central unit, up to an additional seven terminals can be added without a corresponding degradation in performance.

Figure 6:
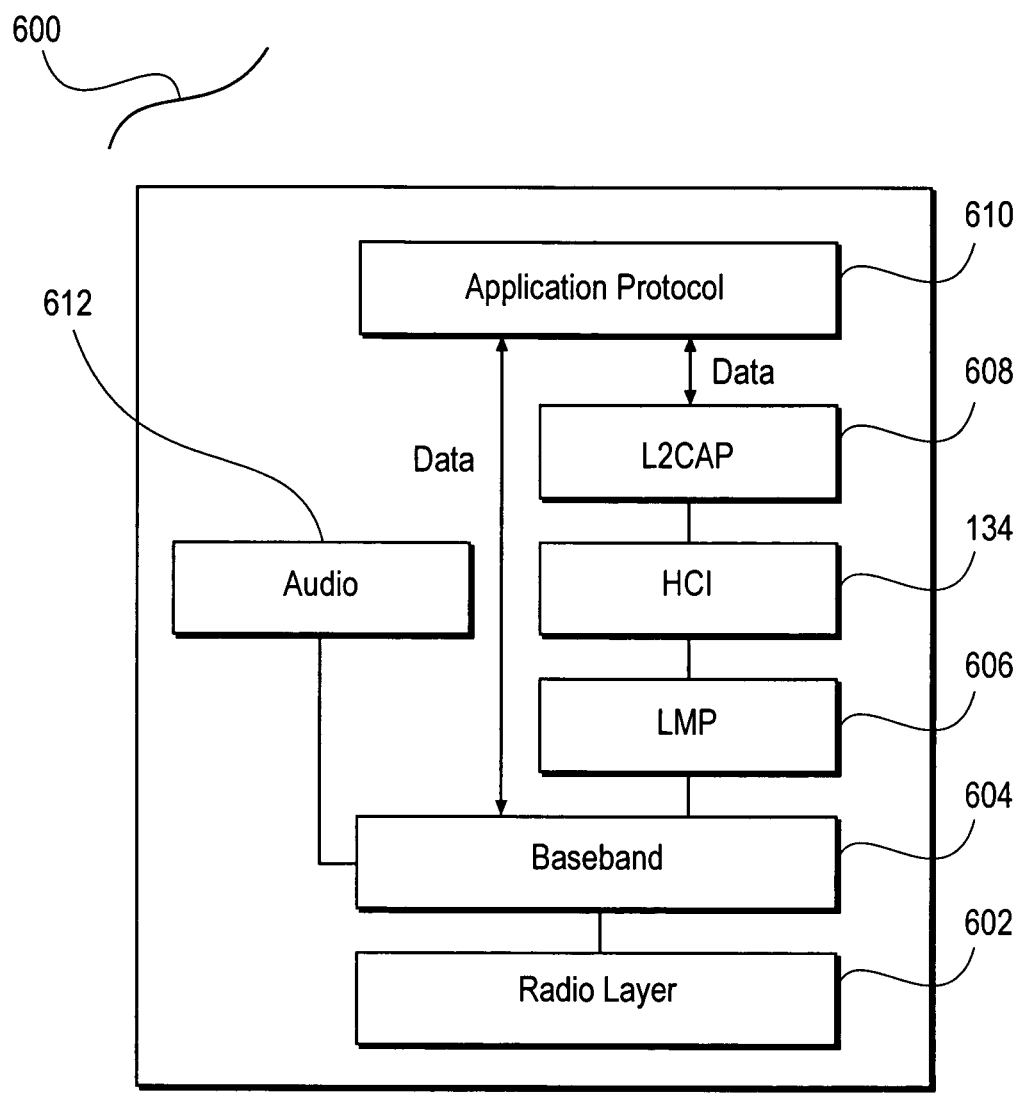
FIG. 6 is a schematic illustration of a protocol stack upon which is based the wireless communication between mobile telemeter, terminals and a central unit, in accordance with an embodiment of the present invention.

Reference is now made to FIG. 6 which illustrates a protocol stack 600 upon which is based the wireless communication between mobile telemeter 108, terminals 186 and central unit 184, in accordance with an embodiment of the present invention. In an embodiment of the invention, protocol stack 600 may include a radio layer 602 which conforms to the physical connection interface. The Bluetooth radio layer 602 is the lowest defined layer of the Bluetooth specification. It defines requirements of the Bluetooth chip transceiver operating in the 2.4 GHz ISM band. Baseband 604 and link manager protocol (LMP) 606 reside over the radio layer 602 and may, in an embodiment, establish and control links with the controller 140 as is depicted in FIG. 1C. Each of radio layer 602, baseband 604 and link manager protocol 606 are included as standard components in many commercially available Bluetooth transceivers which in certain embodiments may be used as controller 140 as is shown in FIG. 1C controller 140, interfaces between the upper application protocol 610 and the Bluetooth chipset transceiver 142 components which include radio layer 602, baseband 604 and link manager protocol 606.

In a typical embodiment of the present invention, radio layer 602 may operate in the unlicensed ISM band and use spread spectrum communication, though operation in other available broadcast bands is also possible. CVSD coding may also be adopted in certain embodiments to withstand high bit error rates. In addition, packet headers may be protected by a highly redundant error correction scheme to make them robust to errors. In a typical embodiment, frequency hops may be fixed at 2402+k MHz, where k=0, 1, 2, . . . , 78. A normal hop rate in a typical embodiment of the invention may be around 1600 hops per second, providing single hop slot of 625 microseconds. In a typical embodiment, the modulation used is Gaussian prefiltered Binary FSK, and power may be set at 0 dBm for 10 m range. Other configurations of such settings are possible in accordance with local licensing requirements and the power needs of particular installations of the present invention. Other frequencies and other data formats may be used.

In a typical embodiment of the invention, baseband 604 controls radio layer 602 and provides the frequency hops. Baseband 604 may in a typical embodiment handle SCO (Synchronous Connection Oriented) and ACL links, where the SCO link mainly carries voice information.

In a typical embodiment baseband layer 604 may also manage packet transmission over wireless links. The SCO packets are used for 64 kB/sec speech transmission. In a typical embodiment, Bluetooth audio resources like Handset Profile and Intercom Profile support the audio layer 612. ACL link may be used for data transfer. In a typical embodiment, baseband 604 may provide functionality required to synchronize clocks of the various components of the present invention and establish connections between them.

Link manager protocol 606 provides piconet management, link configuration and security. Logical link control and adaptation protocol (L2CAP) 608 provides interaction between application protocol 610 and controller interface (HCI) 134 as is depicted in FIG. 1C. In certain embodiments, L2CAP provides multiplexing capabilities to controller 140 so that the controller 140 may communicate with more than one device simultaneously. L2CAP 608 may also reduce the size of packets provided by applications to the size of packets accepted by baseband 604. For example, L2CAP 608 may in certain embodiments accept packet sizes up to 64 Kbits, whereas baseband 604 may be capable of accepting packets of 2,745 bits. L2CAP 608 may also be capable of combining segmented packets into the proper order. Additionally, L2CAP 608 may be configured to manage quality of service functions for controller 140 and Bluetooth chipset transceiver 142 by monitoring peak bandwidth, latency and delay variation. L2CAP 608 may in such case determine the quality of service that the wireless link is capable of providing and configure the transmission of data accordingly. In other embodiments, other modules or sets of modules may control data transmission. Furthermore, functionality of various modules may be combined into other modules.

Controller interface 134 may be used when logical link control and adaptation protocol 608 resides in software in the controller 140. In many commercially available transceiver modules, such as the BlueCore2 from Cambridge Silicon Radio, the logical link control and adaptation protocol 608 are included in the transceiver module. In such case, the controller interface 134 may not be necessary since the Logical link control and adaptation protocol 608 can directly communicate with link manager protocol 606 and baseband 604.

To support person 201 mobility within coverage area 200, terminal 186 and mobile telemeter 108 may in certain embodiments implement a "switch-over" protocol in which the mobile telemeter 108 continuously attempts to establish a wireless connection with terminal 186. In such embodiments, as mobile telemeter 108 comes into transmission range of a particular terminal 186, it will attempt to establish a wireless link with such terminal 186.

In certain embodiments, mobile telemeter 108 may operate in various states such as a "standby state" and a "transmit state". Other states are of course possible. In the standby state, mobile telemeter 108 may operate at a default low power state such that it monitors physiological data from sensors 102, but activates few of its transmission functions. In standby state it may be possible to keep the native clock of the mobile telemeter 108 active, with the remainder of the transmit and receive functions inactive.

When in "transmit state", terminal 186 and mobile telemeter 108 exchange transmission of data. In certain embodiments of the present invention, the wireless link between mobile telemeter 108 and terminal 186 is established during inquiry and paging procedures. Transmit state may be initiated with a poll packet sent by terminal 186 to verify that the mobile telemeter 108 has switched to the timing and channel frequency hopping pattern of terminal 186.

When in "transmit state", mobile telemeter 108 may also be in any of several states including, for example, active and park mode. In active mode, mobile telemeter 108 actively monitors and transmits on the selected channel, and may support regular transmission to keep the terminal 186 synchronized to the channel and to send data to the terminal 186. When in park mode, mobile telemeter 108 may remain synchronized to the channel in which mobile telemeter 108 is transmitting, but it may not participate in the transmission or reception of data traffic. The parked mobile telemeter 108 may occasionally monitor the transmission to synchronize its clock and check on broadcast messages from terminal 186. The park state typically has a low duty cycle and high power efficiency. Other statuses and variations of the readiness of the mobile telemeter 108 and terminal 186 are also possible and result in varying power efficiencies and transmission monitoring benefits.

In certain embodiments of the present invention, mobile telemeter 108 can be set to operate in one of several monitoring methods including "real time monitoring" and "event activated monitoring". Real time monitoring implies that terminal 186 continuously saves physiological data in a buffer of its data storage unit 138 as is depicted in FIG. 1C, and periodically transmits the contents of the buffer data via the terminal 186 to central unit 184 for further processing and or retransmission. This setting lets a continuous flow of physiological data be transmitted to central station 218. In "event activated monitoring" mobile telemeter 108 or terminal 186 may be set to process and analyze physiological data in real time or at preset intervals and store certain limited portions of physiological data in a refreshable loop memory buffer of data storage unit 138. Other modes of operation are possible.

Figure 7A:
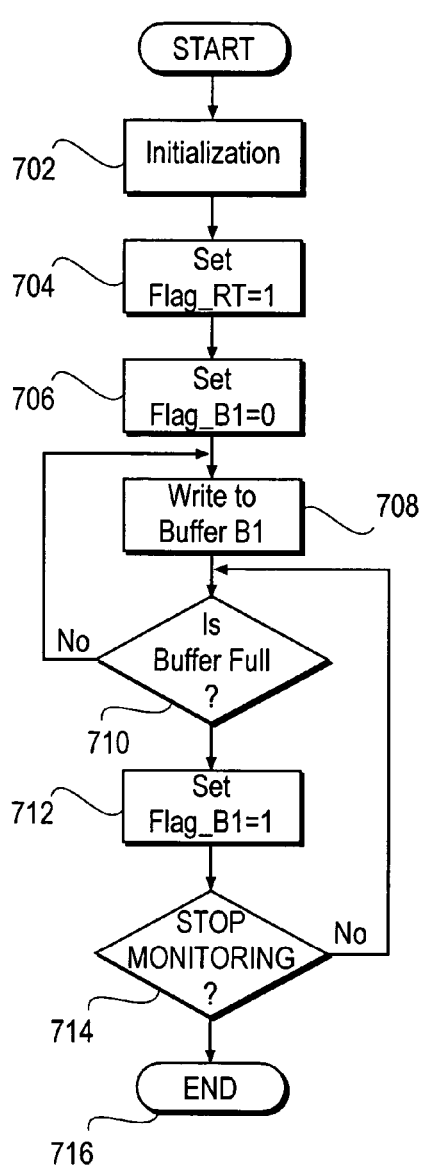
FIG. 7A is a flow chart of a data collection task for real time monitoring by a mobile telemeter in accordance with an embodiment of the present invention.
Figure 7B:
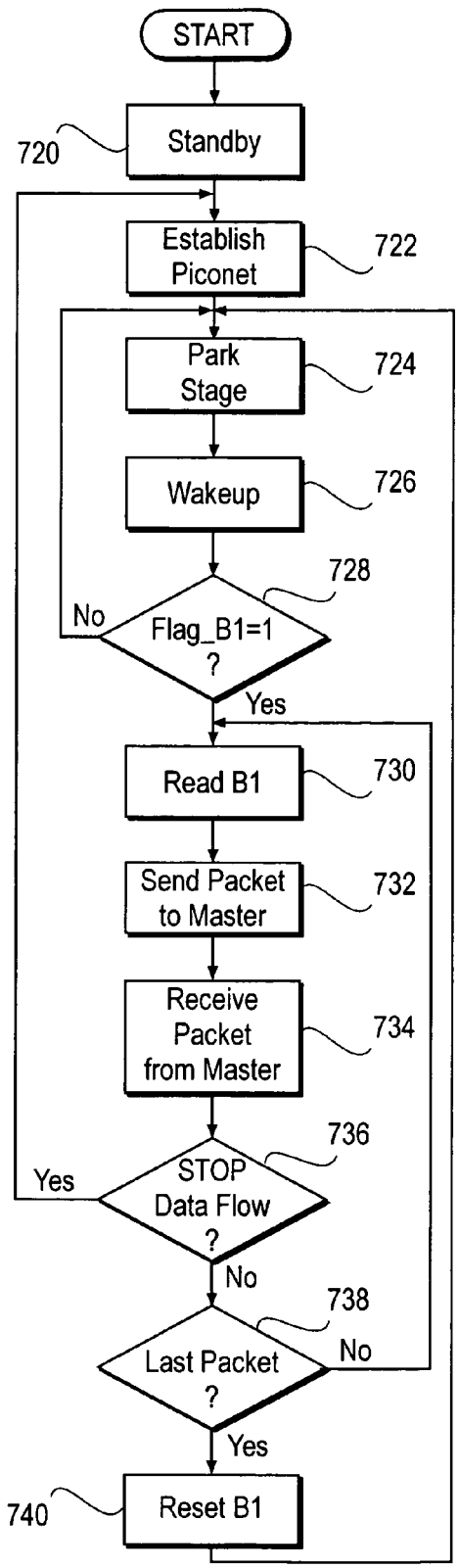
FIG. 7B is a flow chart of a data transmission task for real time monitoring by a mobile telemeter in accordance with an embodiment of the present invention.

FIG. 7A is a flow chart of a data collection task for real time monitoring by a mobile telemeter 108 in accordance with an embodiment of the present invention. FIG. 7B shows a data transmission task for real time monitoring by a mobile telemeter 108 in accordance with an embodiment of the present invention. The data collection task described in FIG. 7A begins with an initialization stage 702, wherein the real time monitoring mode "set Flag_RT"=1 704, memory buffer is set to zero 706 and "Write to buffer B1" 708 routine is activated. "Write to Buffer B1" 708 routine cycles until the "Buffer Full" indicator is detected 710. When the buffer full indicator is detected 710, another routine sets the "Flag_B1" to 1 712 and the content of the buffer B1 is transmitted to terminal 186 in the transmission process described in FIG. 7B. If for some reason the sensor is directed to stop monitoring 714, the data collection task ends 716.

Other steps or series of steps may be used.

As depicted in FIG. 7B, data transmission mode starts with terminal 186 in standby mode 720 until a wireless link is established with another transceiver 722 such as a mobile telemeter 108. Terminal 186 periodically wakes up 726 the transceiver module of mobile telemeter 108 (which may have theretofore been in park state) and checks on Flag B1 as described in reference numeral 712 of FIG. 7A. If Flag B1=1 728, the controller 140 (as depicted in FIG. 1C) of mobile telemeter 108 reads its buffer 730 and sends data 732 to the terminal. Mobile telemeter 108 receives a polling packet from master 732. Terminal 186 checks to see if data has stopped flowing 736 from mobile telemeter 108. If data has stopped flowing, terminal 186 checks to see whether a last packet indicator has been received 738 from the mobile telemeter 108 to indicate that the transmission has ended. If no such indicator has been received even though the data has stopped flowing, there may have been a failure in the communication link. In such event, once the communication link is re-established, the data in Buffer B1 that was incompletely transmitted is transmitted again to the terminal 186.

The amount of time that incompletely transmitted data can remain in Buffer B1 depends on several factors including the amount of memory available in data storage unit 138 and the volume of data being delivered to such data storage unit 138 by the relevant sensor 186. Once the last packet has been received 738 and all data in Buffer B1 has been transmitted to terminal 186, buffer B1 can be reset 740 for further data collection. Other steps or series of steps may be used.

The data collection and data transmission process described in FIGS. 7A and 7B may run independently or simultaneously.

Figure 8A:
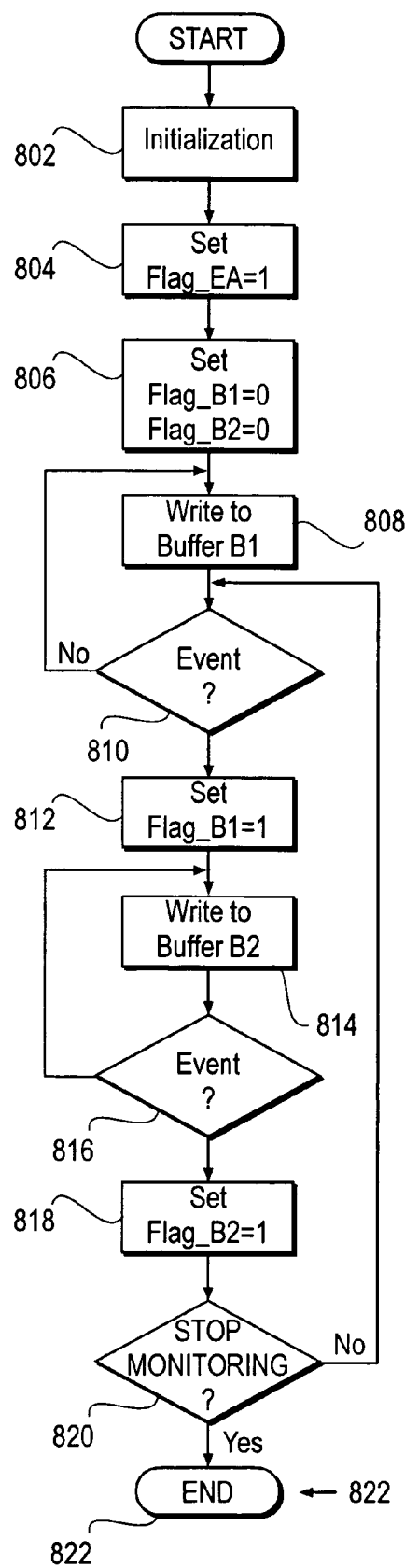
FIG. 8A is a flow chart of a data collection task for event activated monitoring by a mobile telemeter in accordance with an embodiment of the present invention.
Figure 8B:
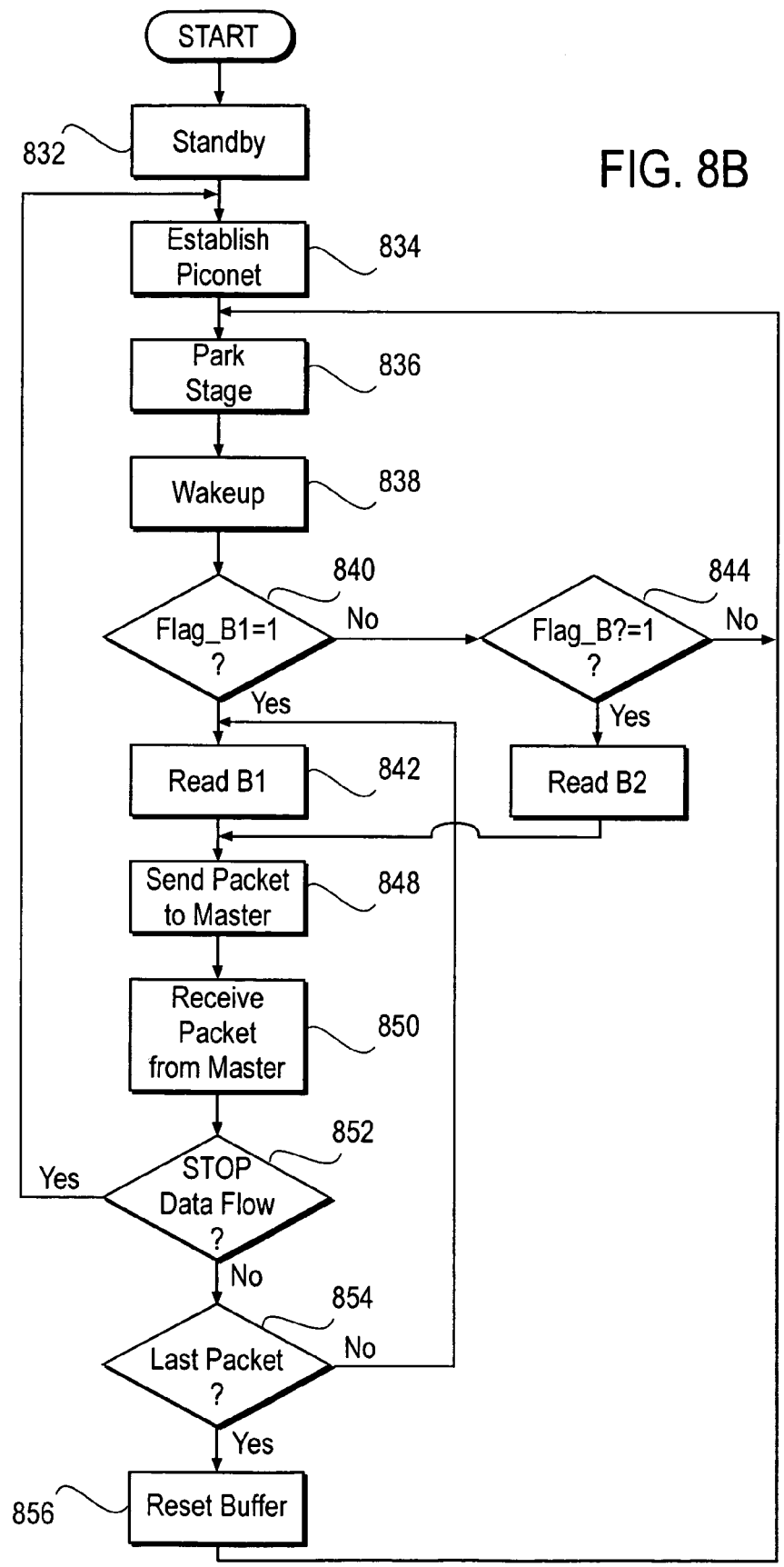
FIG. 8B is a flow chart of a data transmission task for event activated monitoring by a mobile telemeter in accordance with an embodiment of the present invention.

FIG. 8A is a flow chart of a data collection task for "event activated monitoring" by a mobile telemeter 108 in accordance with an embodiment of the present invention. FIG. 8B shows a data transmission task for event activated monitoring by a mobile telemeter 108 in accordance with an embodiment of the present invention. The data collection task in FIG. 8A starts with initialization stage 802 which sets the event activated monitoring mode "Flag_EA"=1 804, resets the memory buffers by setting "Flag_B1"=0 and "Flag_B2"=0 806, and activates the "Write to Buffer B1" routine 808 similar to the routine described in reference numeral 708 of FIG. 7A. This routine may in certain embodiments cycle until the pre-defined event is detected 812. Once the event is detected, the routine sets the "Flag_B1=1" 812 and switches to writing to buffer B2 routine 814.

The content of buffer B1 will be sent to terminal in the data transmission task described in FIG. 8B below. The writing to buffer B2 routine 814 cycles until the next pre-defined event occurs 816 which sets the "Flag_B2=1" 818 and switches the mobile telemeter 108 back to writing to Buffer B1 818. Once Flag B2 is set to 1, the content of Buffer B2 will be sent to terminal 186 in the data transmission task described in FIG. 8B. If stop monitoring indicator is detected 820, the monitoring process is ended 822.

The data transmission task described in FIG. 8B starts with the Bluetooth chipset transceiver 140 of the mobile telemeter 108 (as is depicted in FIG. 1C) in standby stage 832. A wireless link between mobile telemeter 108 as slave and terminal 186 as master is established 834 and mobile telemeter 108 is set in the parked stage 836. Terminal 186 periodically wakes up 838 mobile telemeter 108 and checks the "Flag_B1" 840. If "Flag_B1=1" the routine read Buffer B1 is activated 842. If "Flag_B=0" and "Flag_B2=1" 844, the routine read Buffer B2 846 is activated, sends packet to the terminal 848, receives the packet from master 850 and checks 852 the "STOP data flow" indicator. If "STOP data flow" indicator 852 is not received, the "LAST Packet" indicator is checked 854. The transmission process cycles until the "LAST Packet" is detected. At this stage buffers B1 or B2 is reset 856 and the device is switched to the Parked Stage 836. Receiving "STOP data flow" indicator means a failure has occurred in the wireless link. At that point the mobile telemeter 108 attempts to re-establish the wireless link 834.

Other steps or series of steps may be used.

Figure 9:
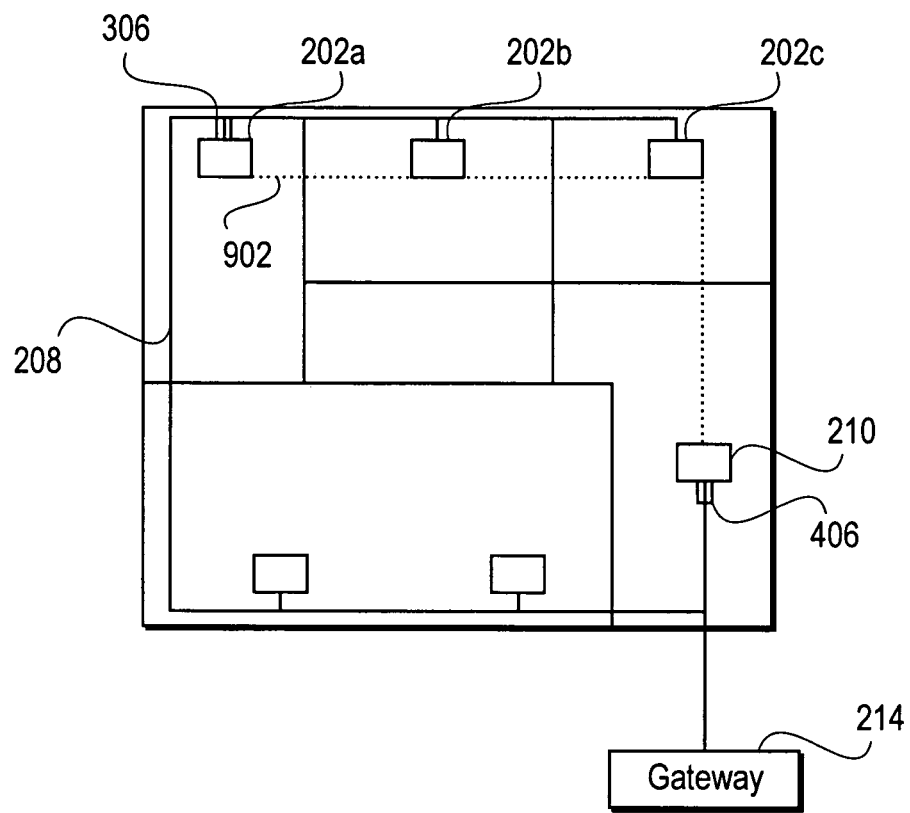
FIG. 9 is a schematic diagram of two possible paths of data signals between terminals and a central unit, in accordance with an embodiment of the present invention.

Reference is made to FIG. 9 which is a schematic diagram of two possible paths of data signals between terminals 186 and central unit 184, in accordance with an embodiment of the present invention. Other signal paths may be used. When wireless communication is available, terminal 186a may transmit signals to terminal 186b using wireless signals 902 illustrated by dashed lines. Terminal 186b may then, for example, relay such signals 902 to terminal 186c which may further relay signals to central unit 184. When wireless communication becomes unavailable for reasons such as, for example, multi-path interference or technical failure of a transceiver, terminal 186a may, for example, transmit data signals by way of power line modem 306 that is included in terminal 186 and the power line modem 406 that is included in central unit 184 over power lines 208 to which both terminals 186 and central unit 210 are connected.

Figure 10:
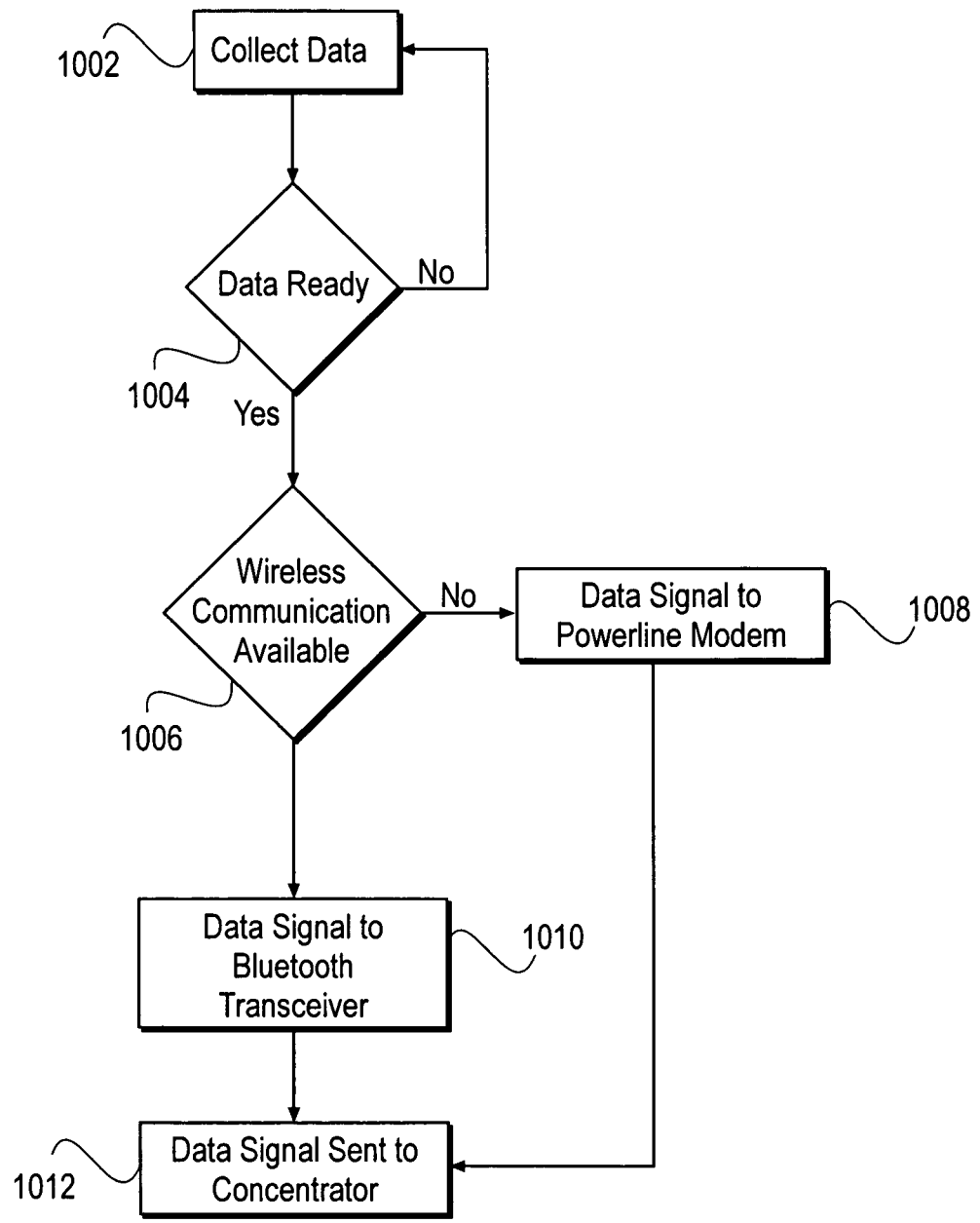
FIG. 10 is a simplified flow chart of the process of determining the communication path by which data signals may be transmitted between an terminal and a central unit.

Reference is made to FIG. 10 which is a simplified flow chart of the process implemented by controller 304 or other components of terminal 186 in determining the communication path by which data signals may be sent between terminal 186 and central unit 184.

In step 1002 terminal 186 collects data from, for example a mobile telemeter 108. Terminal 186 may then determine that data is ready to be transmitted by terminal 186 in step 1004 or that more data is to be collected before initiating such transmission. In step 1006 terminal may poll other terminals 186 or central unit 184 to determine whether a wireless communication link is available for transmission of data signals or whether no such wireless communication link is available. If a wireless communication link can be established then terminal 186 transmits the data signal over such wireless link. If no wireless link can be established, controller 304 or other component of terminal 186 directs the data signal to be sent to central unit 184 over power lines 208 by way of power line modem 306.

Other steps or series of steps may be used.

It will be appreciated by persons skilled in the art that the present invention is not limited to what has been particularly shown and described hereinabove. Rather the scope of the present invention is defined only by the claims which follow.

We claim:

1. A terminal comprising: a wireless transmitter; a wireless receiver, adapted to receive processed physiological data; wherein the processed physiological data is wirelessly transmitted by a wireless telemeter that wirelessly receives physiological data collected by at least one sensor and processes the physiological data to provide the processed physiological data a power line transmitter, coupled to the wireless receiver; a terminal controller, coupled to the power line transmitter and the wireless receiver, for controlling the power line transmitter and the wireless receiver; wherein the terminal controller is adapted to at least partially process the processed physiological data; wherein the process comprises performing health event detection; wherein the terminal controller is further adapted to determine whether to transmit said processed physiological data over the at least one power line or to wirelessly transmit said processed physiological data over a wireless connection; wherein the wireless transmitter is arranged to wirelessly transmit the processed physiological information if it is determined to wirelessly transmit the processed information; wherein the power line transmitter is arranged to transmit, over the at least one power line the processed physiological information if it is determined to wirelessly transmit the processed information over the at least one power line; and wherein the terminal controller is further adapted to determine whether to transmit said processed physiological data over the at least one power line or to wirelessly relay said processed physiological data to another terminal; wherein the wireless transmitter is arranged to wirelessly relay the processed physiological information to another terminal if it is determined to wirelessly relay the processed information to the other terminal.

2. The terminal according to claim 1 whereas the at least one sensor is coupled to a short-range transceiver and whereas the terminal further comprises a wireless transmitter for transmitting signals to the short-range transceiver.

3. The terminal according to claim 1 further adapted to receive physiological data from multiple persons simultaneously.

4. The terminal according to claim 1 whereas the terminal controller is adapted to at least partially analyze the received physiological data and to decide whether to transmit said physiological data.

5. The terminal of claim 1, wherein the terminal functions as a master and the mobile telemeter serves as a slave.

6. The terminal of claim 1, wherein the power line transmitter is coupled to the power line which provides operating power for the terminal and for other devices.

7. The terminal of claim 1, wherein the power line transmitter is coupled to the power line by a common two prong plug via a wall electrical outlet.

8. The terminal of claim 1, wherein the power line transmitter is coupled to the power line by a common three prong plug via a wall electrical outlet.

9. The terminal of claim 1, wherein the power line transmitter is an embedded power line carrier (PLC) modem.

10. The terminal of claim 1, wherein the power line transmitter is adapted to transmit the physiological data over the at least one power line that is a standard residential electric power lines of 110 or 220 volts.

11. The terminal according to claim 1, wherein the terminal controller is adapted to determine, in response to multi-path interference, whether to transmit said processed physiological data over the at least one power line or to wirelessly transmit said processed physiological data over the wireless connection.

12. The terminal according to claim 1, wherein the terminal controller is adapted to determine to transmit said processed physiological data over the at least one power line if wireless communication becomes unavailable.

13. The terminal according to claim 1, wherein the terminal controller is further adapted to determine whether to transmit said processed physiological data over the at least one power line to a central unit or to wirelessly transmit said processed physiological data to the central unit; wherein the wireless transmitter is arranged to wirelessly transmit the processed physiological information to the central unit if it is determined to wirelessly transmit the processed information to the central unit.

14. A terminal comprising:
- a wireless transmitter;
- a wireless receiver, adapted to receive processed physiological data; wherein the processed physiological data is wirelessly transmitted by a wireless telemeter that wirelessly receives physiological data collected by at least one sensor and processes the physiological data to provide the processed physiological data;
- a power line transmitter, coupled to the wireless receiver;
- a terminal controller, coupled to the power line transmitter and the wireless receiver, for controlling the power line transmitter and the wireless receiver;
- wherein the terminal controller is adapted to at least partially process the processed physiological data; wherein the process comprises performing health event detection;
- wherein the terminal controller is further adapted to determine whether to transmit said processed physiological data over the at least one power line or to wirelessly transmit said processed physiological data over a wireless connection;
- wherein the wireless transmitter is arranged to wirelessly transmit the processed physiological information if it is determined to wirelessly transmit the processed information;
- wherein the power line transmitter is arranged to transmit, over the at least one power line the processed physiological information if it is determined to wirelessly transmit the processed information over the at least one power line; and
- wherein the terminal is further adapted to wirelessly receive physiological information from another terminal and to wirelessly relay the physiological information from another terminal to a central unit.

* * * * *